(12) United States Patent
Bechtel et al.

(10) Patent No.: US 11,957,461 B2
(45) Date of Patent: Apr. 16, 2024

(54) ERGONOMIC HANDHELD OXIMETER DEVICE

(71) Applicant: ViOptix, Inc., Newark, CA (US)

(72) Inventors: Kate LeeAnn Bechtel, Pleasant Hill, CA (US); Sophia Elizabeth Berger, Palo Alto, CA (US); Audrey Steever, Fremont, CA (US)

(73) Assignee: ViOptix, Inc., Newark, CA (US)

( * ) Notice: Subject to any disclaimer, the term of this patent is extended or adjusted under 35 U.S.C. 154(b) by 264 days.

(21) Appl. No.: 16/808,308

(22) Filed: Mar. 3, 2020

(65) Prior Publication Data

US 2020/0196929 A1 Jun. 25, 2020

Related U.S. Application Data

(63) Continuation of application No. 15/495,205, filed on Apr. 24, 2017, now Pat. No. 10,575,763.

(60) Provisional application No. 62/326,644, filed on Apr. 22, 2016.

(51) Int. Cl.
*A61B 5/00* (2006.01)
*A61B 5/1455* (2006.01)

(52) U.S. Cl.
CPC ........ *A61B 5/14552* (2013.01); *A61B 5/7221* (2013.01); *A61B 5/742* (2013.01); *A61B 2560/0214* (2013.01); *A61B 2560/0425* (2013.01); *A61B 2560/0475* (2013.01);
(Continued)

(58) Field of Classification Search
CPC . A61B 5/0205; A61B 5/1455; A61B 5/14551; A61B 5/14552; A61B 5/742; A61B 5/7221; A61B 5/681; A61B 2560/0475; A61B 2560/0214; A61B 2560/0425
See application file for complete search history.

(56) References Cited

U.S. PATENT DOCUMENTS

| 5,381,795 A | 1/1995 | Nordgren et al. |
| 6,078,833 A | 6/2000 | Hueber |
| 6,385,821 B1 | 5/2002 | Modgil et al. |

(Continued)

FOREIGN PATENT DOCUMENTS

| EP | 0102816 A2 | 3/1984 |
| EP | 1889569 B1 | 6/2014 |

(Continued)

OTHER PUBLICATIONS

International Search Report, PCT Application PCT/US2017/029196, dated Aug. 3, 2017, 4 pages.

*Primary Examiner* — Chu Chuan Liu
(74) *Attorney, Agent, or Firm* — Aka Chan LLP

(57) ABSTRACT

An oximeter device has an ergonomically shaped enclosure that allows a user to comfortably grip and use the device during handheld operation. A sensor tip can be easily placed evenly on the tissue surface, so that all sources and detectors are directly on the tissue with even pressure. This allows for more consistent and accurate results. The user can easily move the device from one position to another and take numerous measurements. The user will have a wide, unobstructed view of the tissue because of the tip's small size, angle of display, and the grip and fingers are positioned away from the tip. Components housed by the enclosure are arranged to give the device a balanced weighting while in the hand. The device can be used for long periods at a time without fatigue.

32 Claims, 17 Drawing Sheets

(52) U.S. Cl.
CPC ............. *A61B 2562/0238* (2013.01); *A61B 2562/0242* (2013.01); *A61B 2562/046* (2013.01)

(56) References Cited

U.S. PATENT DOCUMENTS

| | | |
|---|---|---|
| 7,236,813 B2 | 6/2007 | Parker |
| 8,233,955 B2 | 7/2012 | Al-ali et al. |
| 8,938,279 B1 | 1/2015 | Heaton, II et al. |
| 2003/0009092 A1 | 1/2003 | Parker |
| 2004/0034294 A1 | 2/2004 | Kimball et al. |
| 2006/0053522 A1 | 3/2006 | Kimbell |
| 2007/0244377 A1 | 10/2007 | Cozad et al. |
| 2008/0287750 A1 | 11/2008 | Hashimshony et al. |
| 2008/0319290 A1 | 12/2008 | Mao et al. |
| 2009/0253968 A1 | 10/2009 | Cho et al. |
| 2010/0005630 A1 | 1/2010 | Gitman et al. |
| 2010/0292549 A1 | 11/2010 | Shuler |
| 2010/0298728 A1 | 11/2010 | Addison et al. |
| 2011/0205535 A1 | 8/2011 | Soller et al. |
| 2011/0224518 A1 | 9/2011 | Tindi et al. |
| 2011/0276276 A1 | 11/2011 | Kashyap et al. |
| 2012/0289801 A1 | 5/2012 | Yamaguchi |
| 2013/0023743 A1 | 1/2013 | Al-ali et al. |
| 2013/0317331 A1 | 11/2013 | Bechtel et al. |
| 2014/0046152 A1 | 2/2014 | Bechtel et al. |
| 2014/0180043 A1 | 6/2014 | Addison et al. |
| 2014/0288386 A1 | 9/2014 | Zand et al. |

FOREIGN PATENT DOCUMENTS

| | | |
|---|---|---|
| WO | 2009090665 A1 | 7/2009 |
| WO | 2010011763 | 1/2010 |
| WO | 2010042264 A1 | 4/2010 |
| WO | 2014026200 | 2/2014 |

ERGONOMIC HANDHELD OXIMETER DEVICE

CROSS-REFERENCE TO RELATED APPLICATIONS

This patent application is a continuation of U.S. patent application Ser. No. 15/495,205, filed Apr. 24, 2017, issued as U.S. Pat. No. 10,575,763 on Mar. 3, 2020, which claims priority to U.S. patent application 62/326,644, filed Apr. 22, 2016, These applications are incorporated by reference along with all other references cited in this application.

BACKGROUND OF THE INVENTION

This invention relates generally to medical devices and more specifically to an ergonomic, handheld oximeter device that monitors oxygen levels in tissue.

In previous tissue oximeter systems, there is a probe that is connected by a cable to a system unit. The system unit is a relatively large and heavy component, which is typically securely held in an equipment bay or by a pole in an exam room along with other medical equipment. The relatively large size of such tissue oximeter systems prevent them from being used in wider range of applications.

Therefore, there is a need for an ergonomic handheld oximeter device in a self-contained unit.

BRIEF SUMMARY OF THE INVENTION

An oximeter device has an ergonomically shaped enclosure that allows a user to comfortably grip and use the device during handheld operation. A sensor tip can be easily placed evenly on the tissue surface, so that all sources and detectors are directly on the tissue with even pressure. This allows for more consistent and accurate results. The user can easily move the device from one position to another and take numerous measurements. The user will have a wide, unobstructed view of the tissue because of the tip's small size, angle of display, and the grip and fingers are positioned away from the tip. Components housed by the enclosure are arranged to give the device a balanced weighting while in the hand. The device can be used for long periods at a time without fatigue.

The oximeter device is a self-contained unit. The enclosure houses a processor to perform oximetry measurements, and batteries to power the electronics, display, and oximeter sensor. The sensor is at a tip of the device and includes sources to emit light and detectors to receive light reflected by a tissue being measured. Based on the emitted and received light, the processor calculates an oxygen saturation value or other oximetry value and displays this on a screen of the device.

The device has a thumb rest, against which the user's thumb will be placed when the device is in use. The thumb is positioned above the sensor tip, which helps provide even pressure from above the sensor tip to the tip when tip is against the tissue being measured. The device has even weight distribution due to an arrangement of the components (e.g., batteries) in the enclosure. The user will be able to see an orientation or positioning of the sensor and see a reading on the screen at the same time.

The device has a single button for use (e.g., for turning on the device). The device has an automatic measurement feature, and no additional action is required. For example, a button press is not needed to make a measurement. The device automatically takes a measurement when the sensor is placed on the tissue. Data collected by the device can be downloaded through a port. A location of the port is behind batteries behind a removable cover of the device, which in an implementation, is the only removable cover.

A specific implementation of an oximeter device is, for example, the Intra.Ox™ Handheld Tissue Oximeter product by Vioptix, Inc. Intra.Ox is a trademark of Vioptix. Intra.Ox can noninvasively estimate the percent oxygen saturation (StO2) in a volume of tissue. Intra.Ox can be used in monitoring patients during circulatory or perfusion examinations.

Intra.Ox allows for instantaneous results in a surgeon's hands. Intra.Ox is a handheld, disposable sensor that provides surgeons with real-time, noninvasive tissue perfusion assessments in three ways: pre-op base line assessment, intra-operative mapping and post-op intensive care unit (ICU) monitoring.

This device provides clinicians the ability to take instantaneous readings throughout the surgery without increasing time in the operating room. It helps facilitate faster intra-operative decisions to improve surgical outcomes and patient satisfaction.

Intra.Ox can be used to benefit patients in connection with a wide variety of procedures including: breast reconstruction; trauma surgeries; total knee replacements; amputations; plastic surgery; bowel resections; kidney and liver transplants; and wound care.

Intra.Ox has a tissue oxygen saturation range (StO2) range from 1 to 99 percent. A time to a first reading is instantaneous. The Intra.Ox takes one measurement and provides one reading at a time. A tissue depth for a measurement is about 1 millimeter to about 3 millimeters. The Intra.Ox emits four different wavelengths of lights, and has four detectors. Power is provided by batteries that provide up to about 6 hours of use.

In an implementation, a device includes a body portion and a tip portion. The body portion includes a rectangular tubular portion having a front side surface and a back side surface, which are connected together by first and second side surfaces. The rectangular tubular portion can include rounded corners. A first distance between the first and second side surfaces can be greater than a second distance between the front and back side surfaces. In another implementation, the body portion includes a cylindrical tubular portion.

The tip portion includes a first finger rest surface (e.g., thumb rest) that is connected to the front side surface. The first finger rest surface is a convex surface that extends at a first angle in a first turn direction (e.g. clockwise direction) relative to the front side surface. The first finger rest surface can be adapted for a thumb of a user.

The tip portion includes a front tip surface that is connected to the first finger rest surface. The front tip surface extends at a second angle in a second turn direction (e.g., counterclockwise direction) relative to the first finger rest surface.

The tip portion includes a bottom face surface that is connected to the front tip surface. The bottom face surface extends at a third angle in the second turn direction relative to the first finger rest surface. And the bottom face surface includes an opening which will retain a sensor head of the device (e.g., holds the sensor head at a particular position on the bottom face).

The tip portion includes a second finger rest finger (e.g., middle finger rest) that is connected to the back side surface. The second finger rest surface is a concave surface that extends at a fourth angle in the first turn direction relative to the back side surface. The second finger rest surface can be adapted for a middle finger of a user.

The tip portion includes a back tip surface that is connected between the second finger rest surface and the bottom face surface. The back tip surface is a convex surface that extends at a fifth angle in the first turn direction relative to the second finger rest surface.

In various implementations, the back side and bottom face surfaces are relatively flat surfaces that are angled relative to each other in a range from 90 degrees to about 150 degrees. A first height of the first finger position above the bottom face surface is greater than a second height of the second finger position above the bottom face surface. The first angle is angled relative to the front side surface in a range from 90 degrees to about 60 degrees.

Batteries can be enclosed within the rectangular tubular portion, and the batteries are closer to the back side surface than the front side surface. This allows the device to have a balanced weighting when gripped by a person using the device.

When the device is gripped by a hand of a user, a thumb of the user will be against the first finger rest surface. A middle finger of the user will be against the first finger rest surface. A webbing between the thumb and a index finger of the user will be against the back side surface.

The sensor head can include a number of sources, the sources are arranged along a line, and a number of detectors. There are an equal number of detectors on either side of this line, and a position of a detector on a first side of the line will have point symmetry with another detector on a second of the line about a selected point on the line. The selected point can be a middle between two sources.

The device can be part of an oximeter system. Further, the device can include: batteries, enclosed within the rectangular tubular portion, where the batteries are closer to the back side surface than the front side surface; sensor head, including an arrangement of source structures and detector structures; a display; and electronics, connected to the battery, sensor head, and display, where the electronics causes light to be transmitted through the source structures of the sensor head, and based on light received through the detector structures, the electronics determines an oxygen saturation value and causes the display to show the oxygen saturation value.

The device can include a sensor head assembly which includes the sensor head. The sensor head assembly is enclosed by a space between the convex surface of the first finger rest surface and the concave surface of the second finger rest surface. In an implementation, instead of a convex surface, the surface includes a concave surface. In an implementation, instead of a convex surface, the surface includes a flat or relatively flat surface. The surface can be convex, concave, or flat, or any combination of these.

In an implementation, a device includes a body portion and tip portion. The body portion includes a tubular portion including a front side surface and a back side surface, connected together by first and second side surfaces. For the tip portion, a first finger rest surface is connected to the front side surface. The first finger rest surface is a convex surface that extends at a first angle in a first turn direction relative to the front side surface. A front tip surface is connected to the first finger rest surface. The front tip surface extends at a second angle in a second turn direction relative to the first finger rest surface.

A bottom face surface is connected to the front tip surface. The bottom face surface extends at a third angle in the second turn direction relative to the first finger rest surface. The bottom face surface includes an opening which will retain a sensor head of the device. A second finger rest finger is connected to the back side surface. The second finger rest surface is a concave surface that extends at a fourth angle in the first turn direction relative to the back side surface. A back tip surface is connected between the second finger rest surface and the bottom face surface. The back tip surface is a convex surface that extends at a fifth angle in the first turn direction relative to the second finger rest surface.

A surface of the device that is described as convex can alternatively be convex or flat (or relatively flat), or any combination of these. A surface of the device that is described as concave can alternatively be concave or flat (or relatively flat), or any combination of these. For example, the surface can include a concave portion and convex portion. The surface can include a concave portion and flat portion. The surface can include a convex portion and flat portion. The surface can include a concave portion, convex portion, and flat portion.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
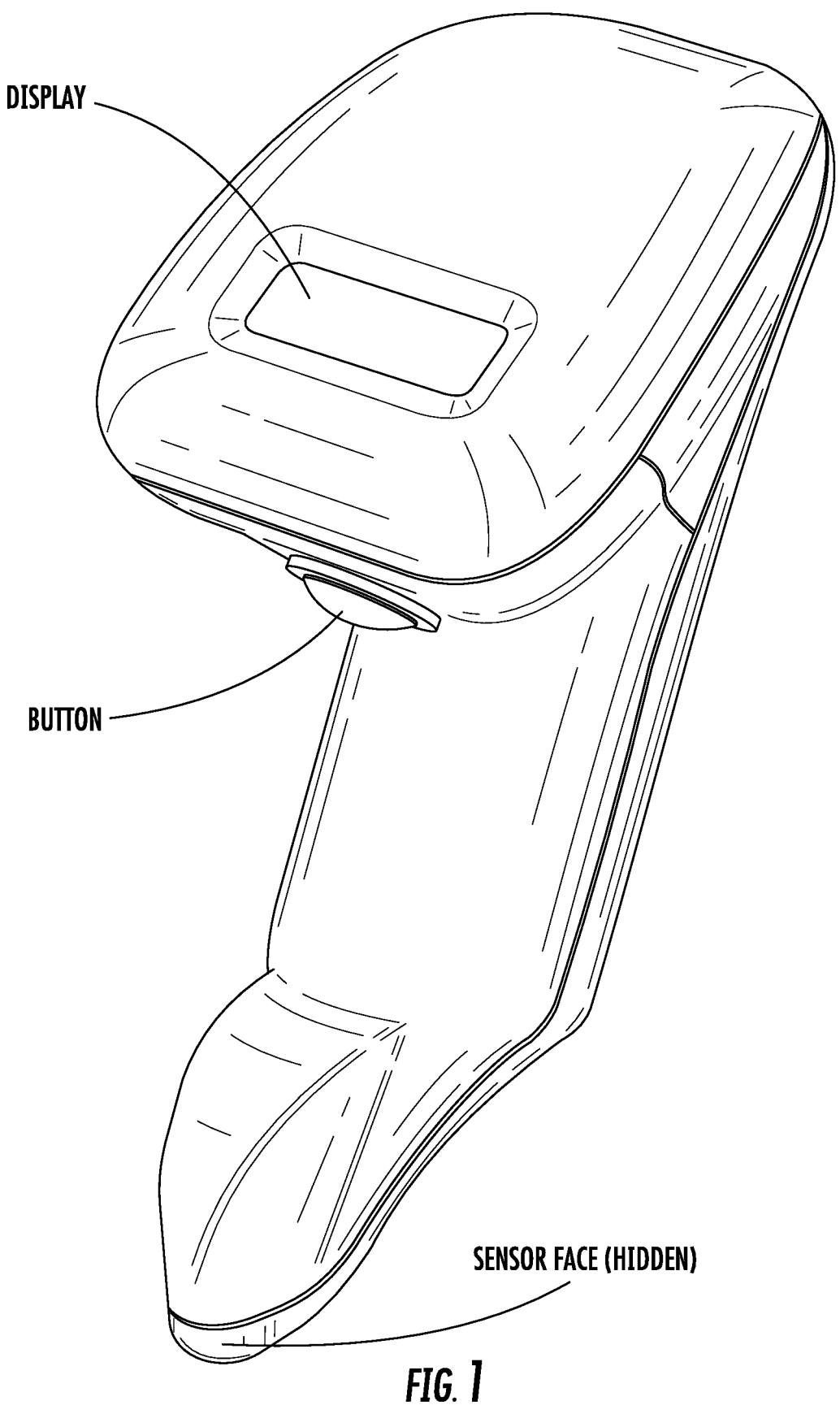
FIG. 1 shows an oximeter device having an ergonomically shaped enclosure.

FIG. 1 shows an oximeter device or oximeter probe having an ergonomically shaped enclosure. The device has a display, button, and sensor face, which is hidden this figure. A specific implementation of the oximeter device is the Intra.Ox Handheld Tissue Oximeter product by ViOptix, Inc. The ViOptix Web site, www.vioptix.com, ViOptix publications (including user guides, specifications, tutorials, videos, and others), patents, patent publications, and other publications about Intra.Ox, T.Ox, T.Ox Remote, and other products existing at the time of the filing of this application are incorporated by reference.

In a specific implementation, Intra.Ox is a sterile, cordless, battery-powered device that noninvasively estimates percent oxygen saturation (StO2) in a volume of tissue. The device uses spatially resolved optical measurements at four wavelengths. The device performs measurements on the patient by direct physical contact to the patient's tissue and displays the StO2 estimate on the device's built-in screen. Intra.Ox is a single-use disposable constructed from biocompatible materials that can tolerate bodily fluids and other liquids such as disinfectants and marking materials.

Intra.Ox can be used in medical environments including doctor or physician offices, hospitals, ambulatory case, and emergency medical services. The device provides medical parameters including tissue oxygen saturation (e.g., percent StO2) and can include a trend graph. The device uses spectrophotometric oximetry. For operation, the device uses near-infrared light, generated by light emitting diode semiconductor integrated circuits at wavelengths of 760, 810, 850, and 900 nanometers. Other wavelengths may be used, such as 690 and 830 nanometers, and many others.

The sensor and a control unit, which controls operation of the sensor, are integrated into a single unit and the entire unit is disposable after use. The device is powered by four lithium AA-size batteries, which have a total battery voltage of 6 volts.

The following U.S. patent applications are incorporated by reference along with all other references cited in this application: Ser. Nos. 15/493,132, 15/493,111, 15/493,121, filed Apr. 20, 2017, Ser. No. 15/494,444, filed Apr. 21, 2017, Ser. Nos. 15/495,194 and 15/495,212, filed Apr. 24, 2017, 62/363,562, filed Jul. 18, 2016; 62/326,673 and 62/326,630, filed Apr. 22, 2016; 62/325,919, filed Apr. 21, 2016; 62/325, 403, 62/325,413, 62/325,416, filed Apr. 20, 2016; Ser. No. 29/561,749, filed Apr. 19, 2016; Ser. Nos. 13/887,130, 13/887,220, 13/887,213, 13/887,178, 13/965,156, and 13/887,152, filed May 3, 2013; and 61/642,389, 61/642,393, 61/642,395, 61/642,399, 61/682,146, filed May 5, 2012. The above applications describe various oximeter devices and oximetry techniques, and the discussion in the above applications can be combined with aspects of the invention described in this application, in any combination.

Figure 2:
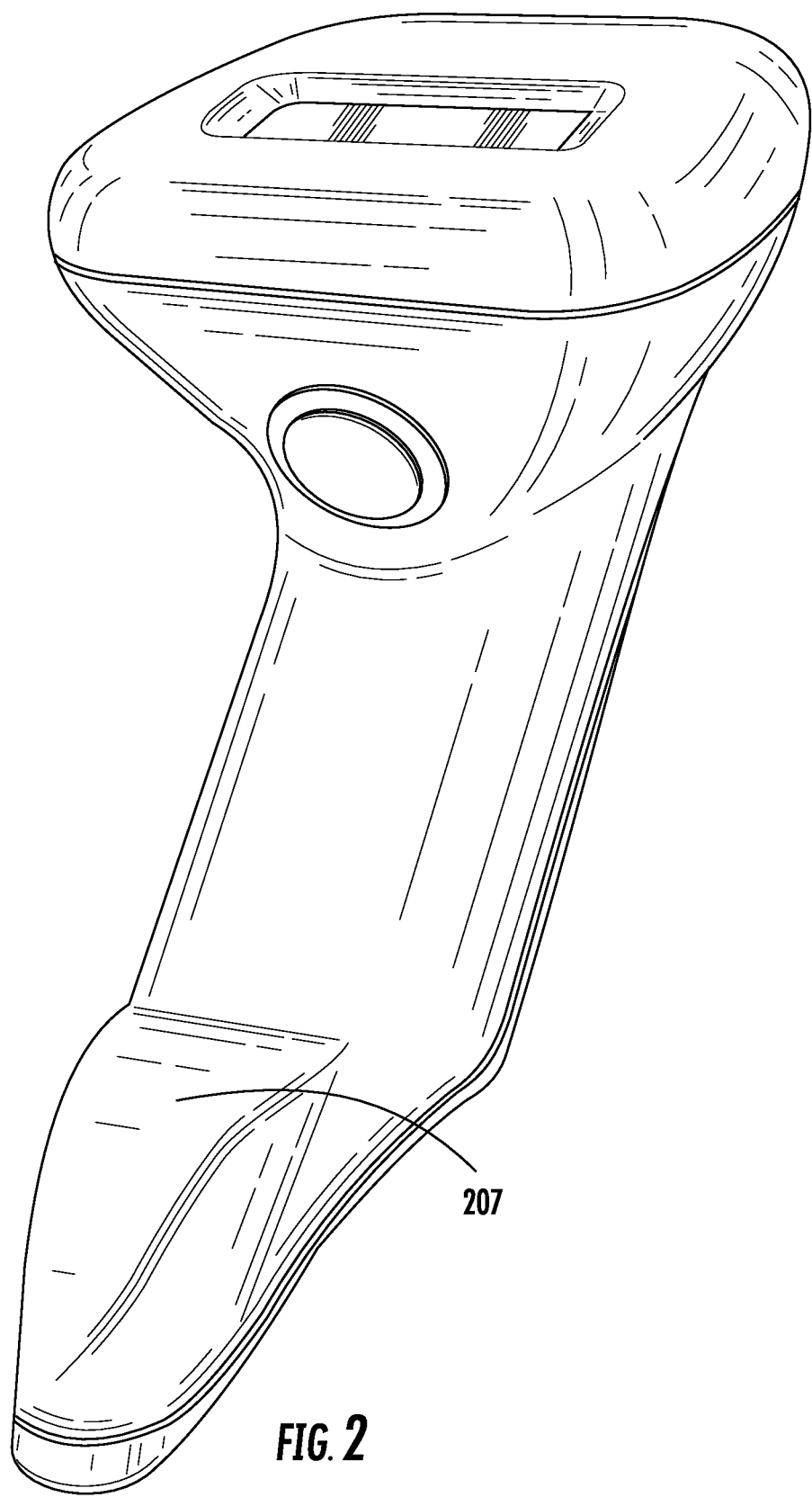
FIG. 2 shows a perspective view of the oximeter device.
Figure 3:
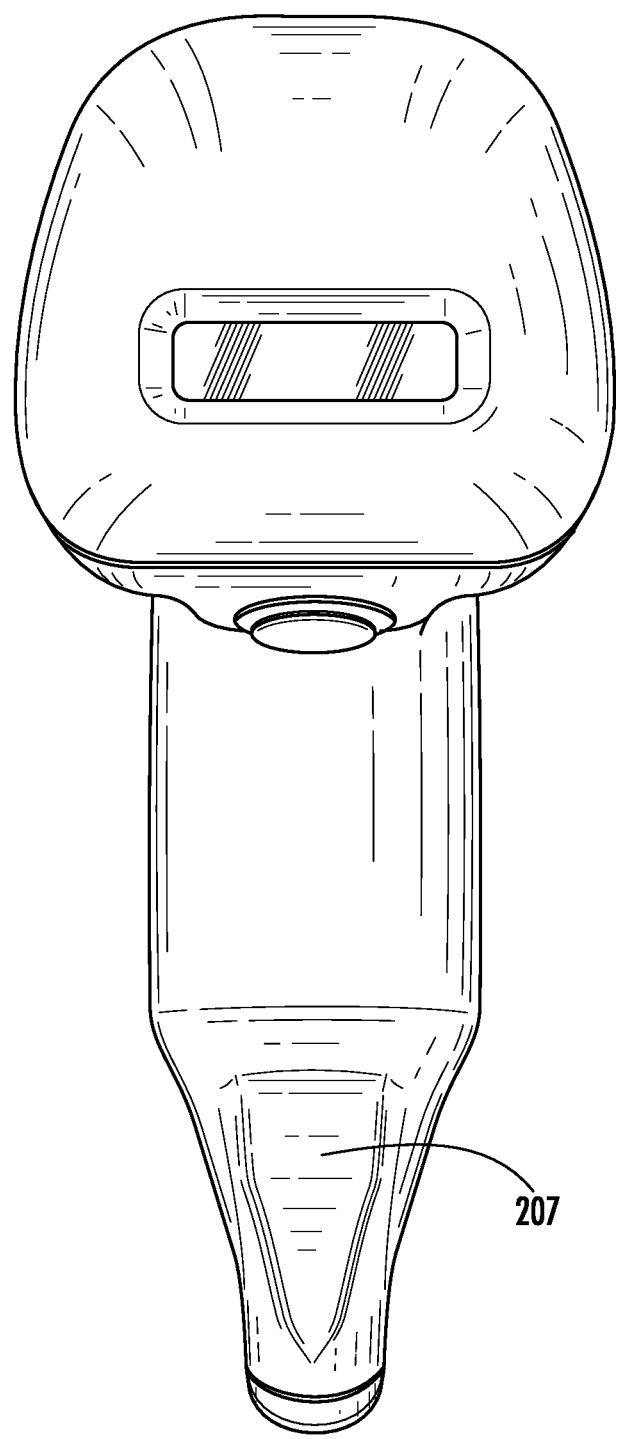
FIG. 3 shows a front view of the oximeter device.
Figure 4:
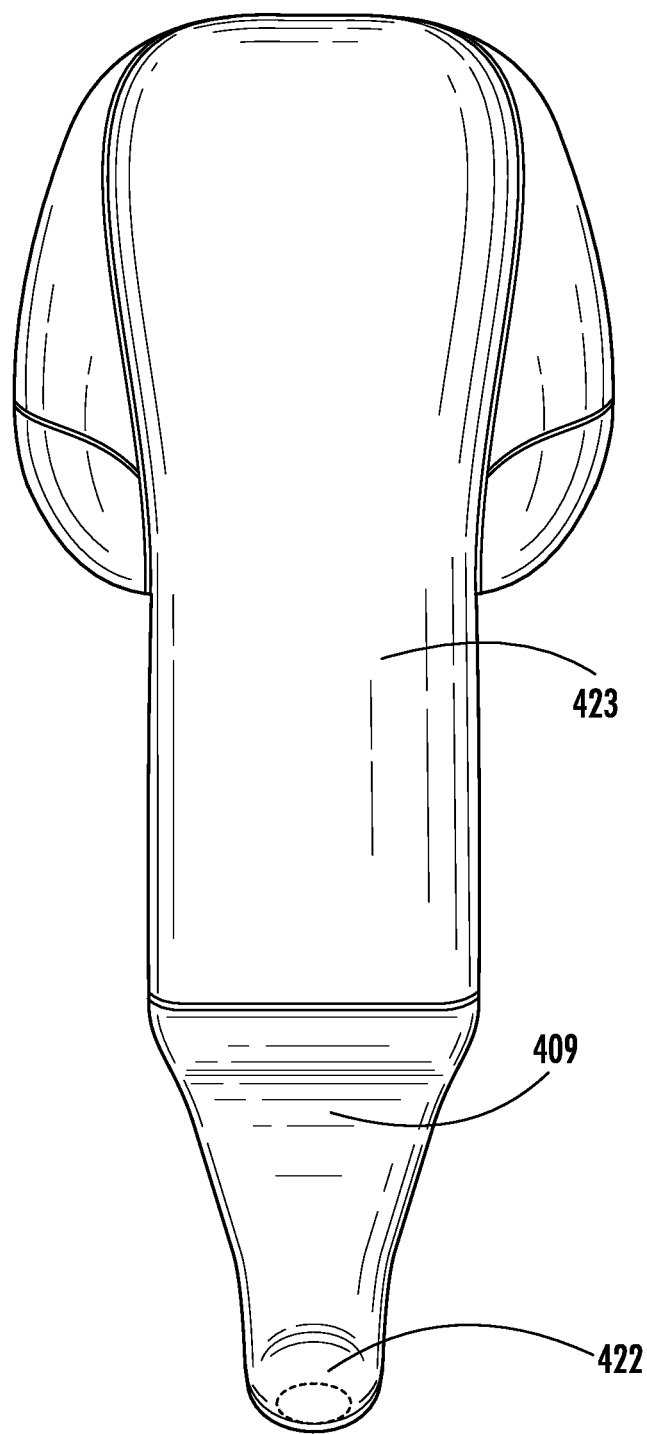
FIG. 4 shows a back view of the oximeter device.
Figure 5:
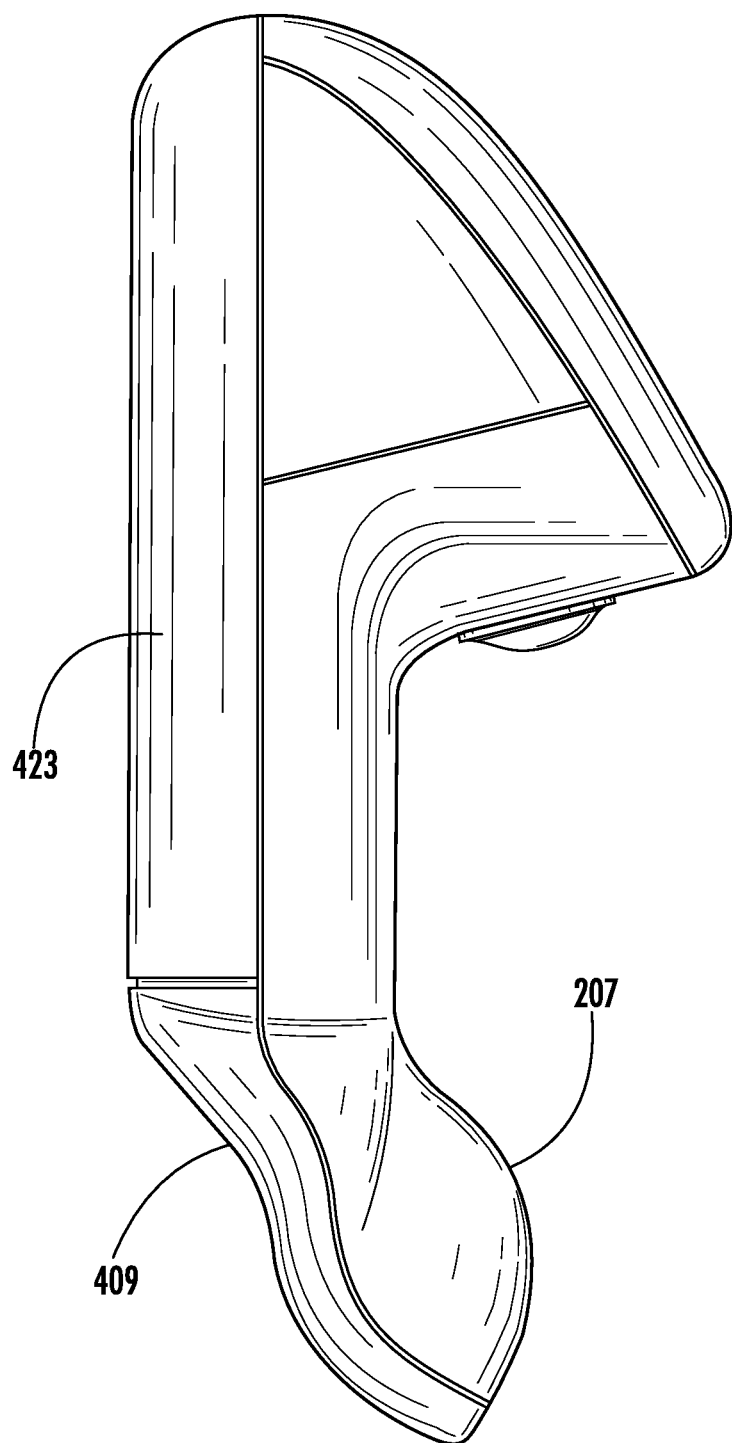
FIG. 5 shows a left side view of the oximeter device.
Figure 6:
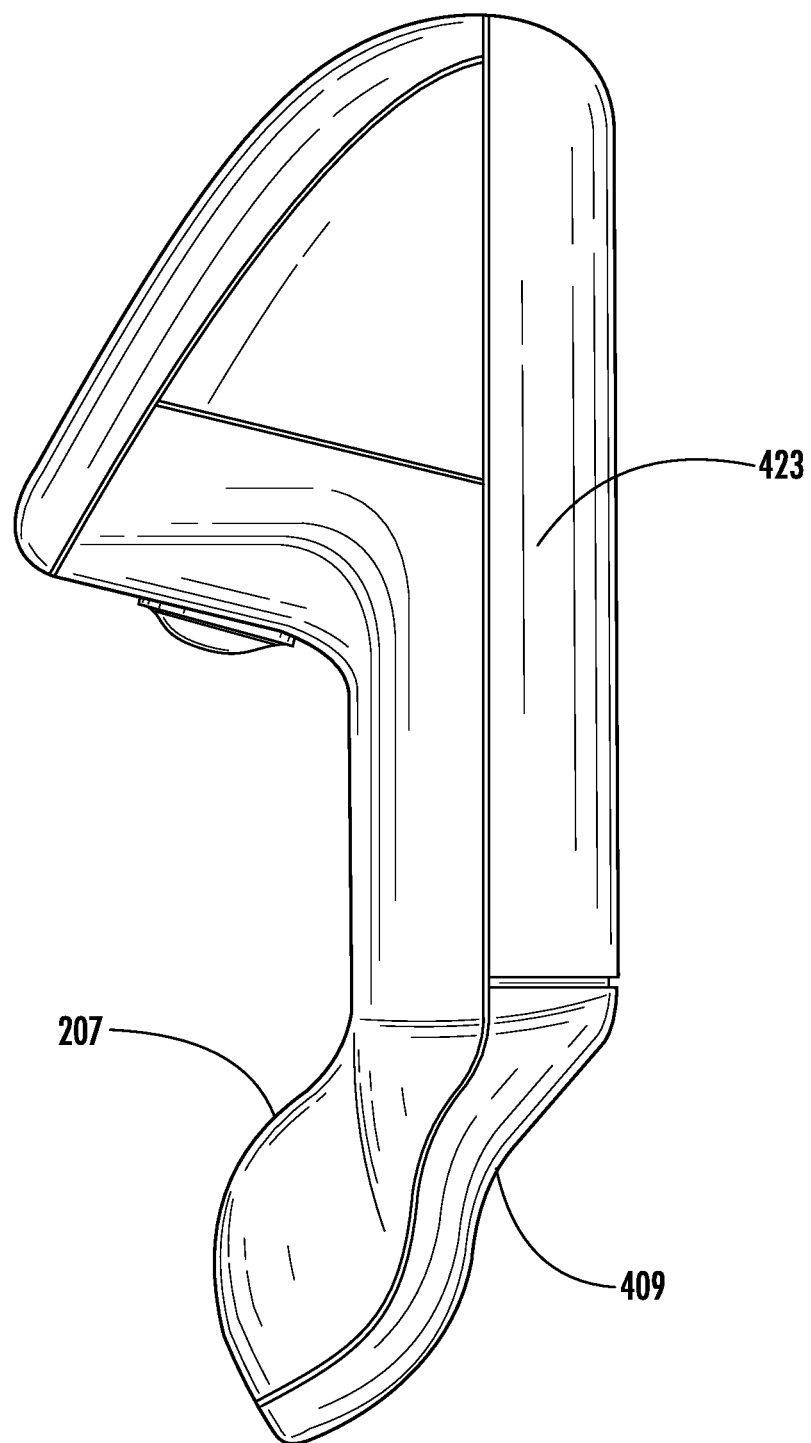
FIG. 6 shows a right side view of the oximeter device.
Figure 7:
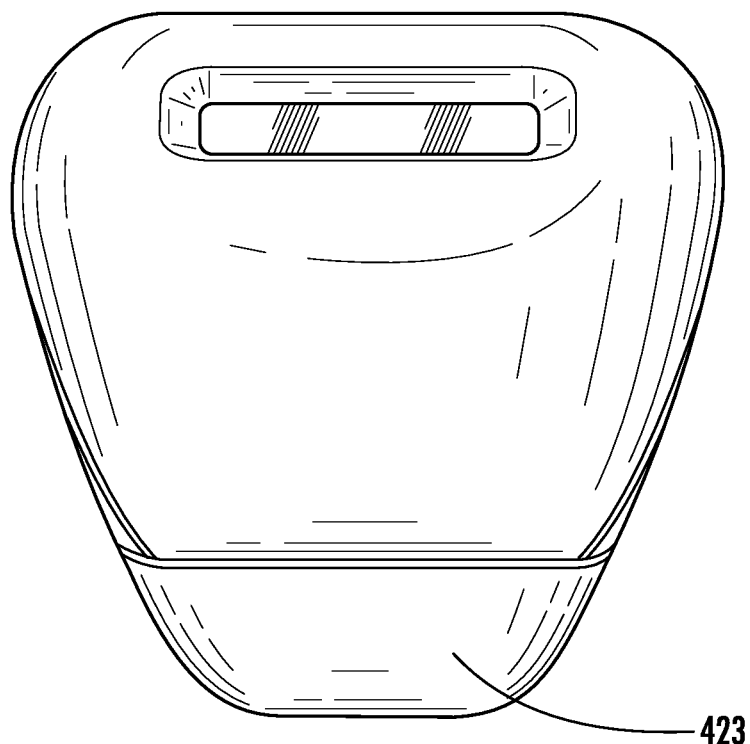
FIG. 7 shows a top view of the oximeter device.
Figure 8:
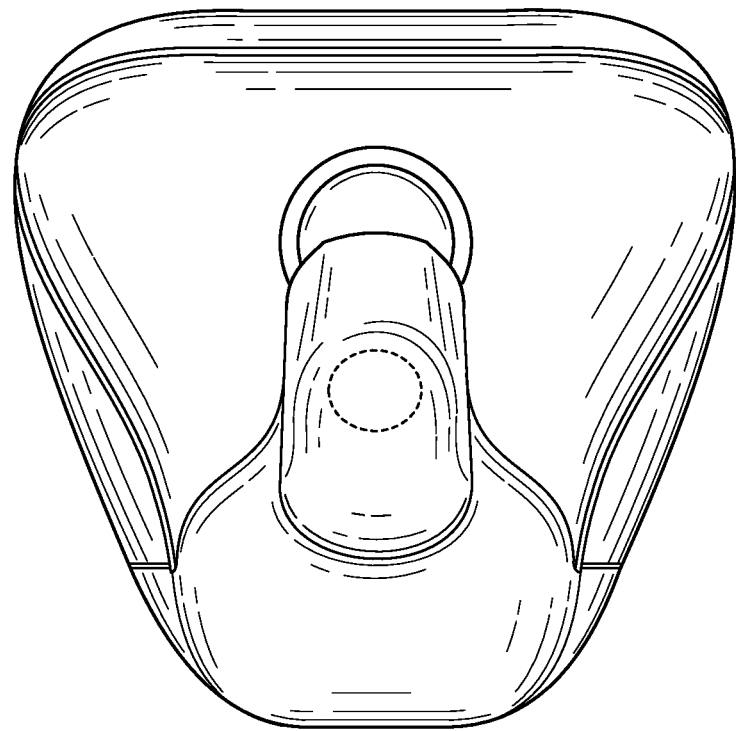
FIG. 8 shows a bottom view of the oximeter device.
Figure 9:
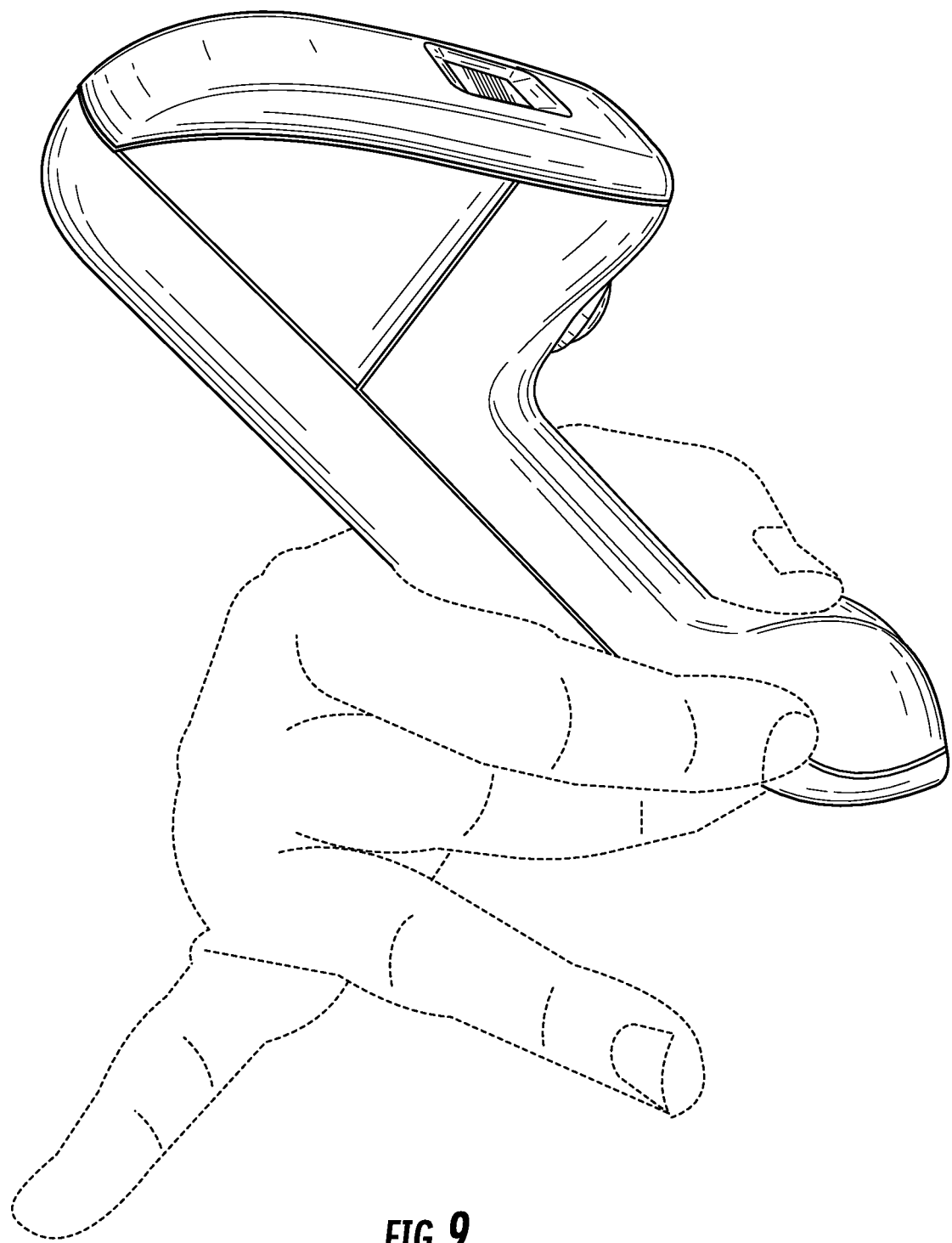
FIG. 9 shows the oximeter device in use, being gripped by a hand of a user

FIGS. 2-9 show various views of the oximeter device. FIG. 2 shows a perspective view. FIG. 3 shows a front view. FIG. 4 shows a back view. FIG. 5 shows a left side view. FIG. 6 shows a right side view. FIG. 7 shows a top view. FIG. 8 shows a bottom view. FIG. 9 shows the device in use, being gripped by a hand of a user.

The device has a thumb rest 207 and a middle finger rest 409. The thumb rest is a portion of the device against which the thumb will be placed against. The middle finger rest is a portion of the device against which the middle finger will be placed against.

Figure 10:
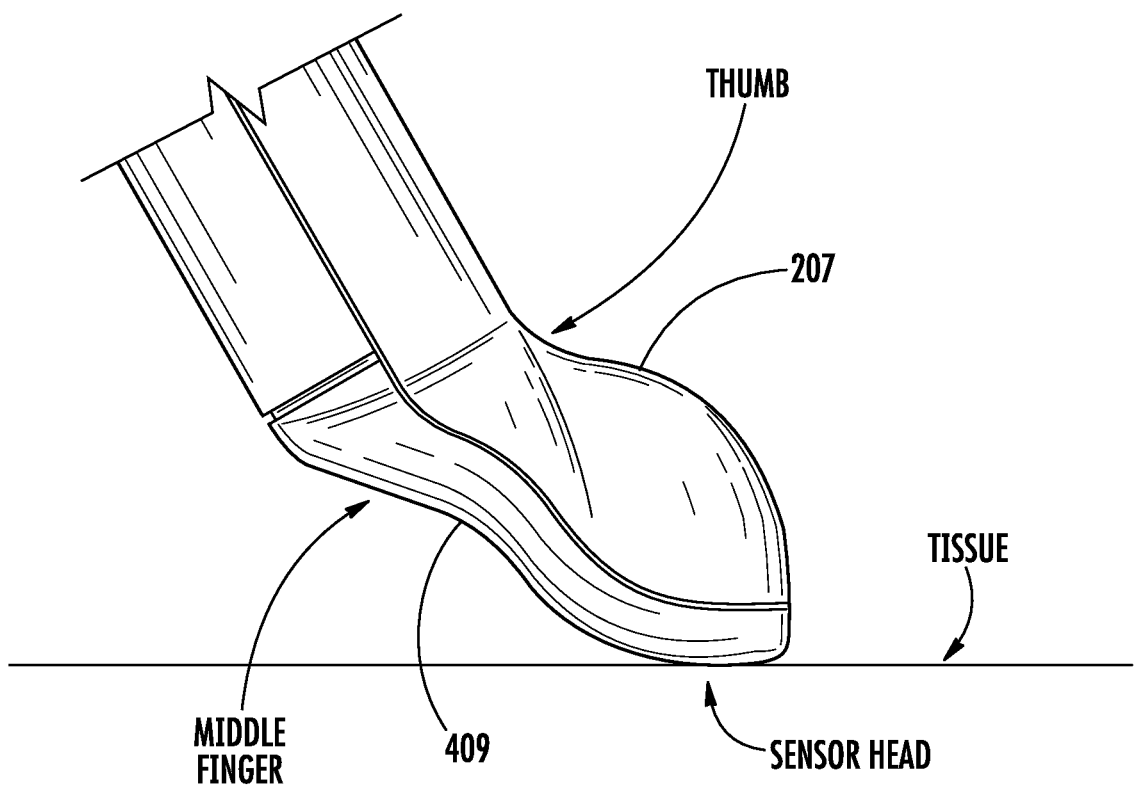
FIG. 10 shows a portion of the oximeter device and grip positions of the thumb rest and middle finger rest.

FIG. 10 shows a portion of the oximeter device and grip positions of the thumb rest and middle finger rest. A sensor head of the oximeter tip is placed against tissue surface. The sensor head makes contact with the tissue.

Referring to FIGS. 9 and 10, when the oximeter is gripped by a hand, the user's thumb is placed against the thumb rest, which is beneath or below the thumb. The user's middle finger is placed against the middle finger rest, which is above the middle finger. The middle finger supports the weight of the oximeter. A back of the device rests against the webbing between the thumb and index finger, which cradles the device.

With the thumb positioned on the thumb rest, pressure from the thumb is applied from above the sensor tip to provide even pressure for the sensor head to contact the tissue being measured. All sources and detectors of the sensor will be against the tissue surface, so the sensor will have full contact with the tissue surface. This allows for more consistent and accurate sensor readings.

Figure 11:
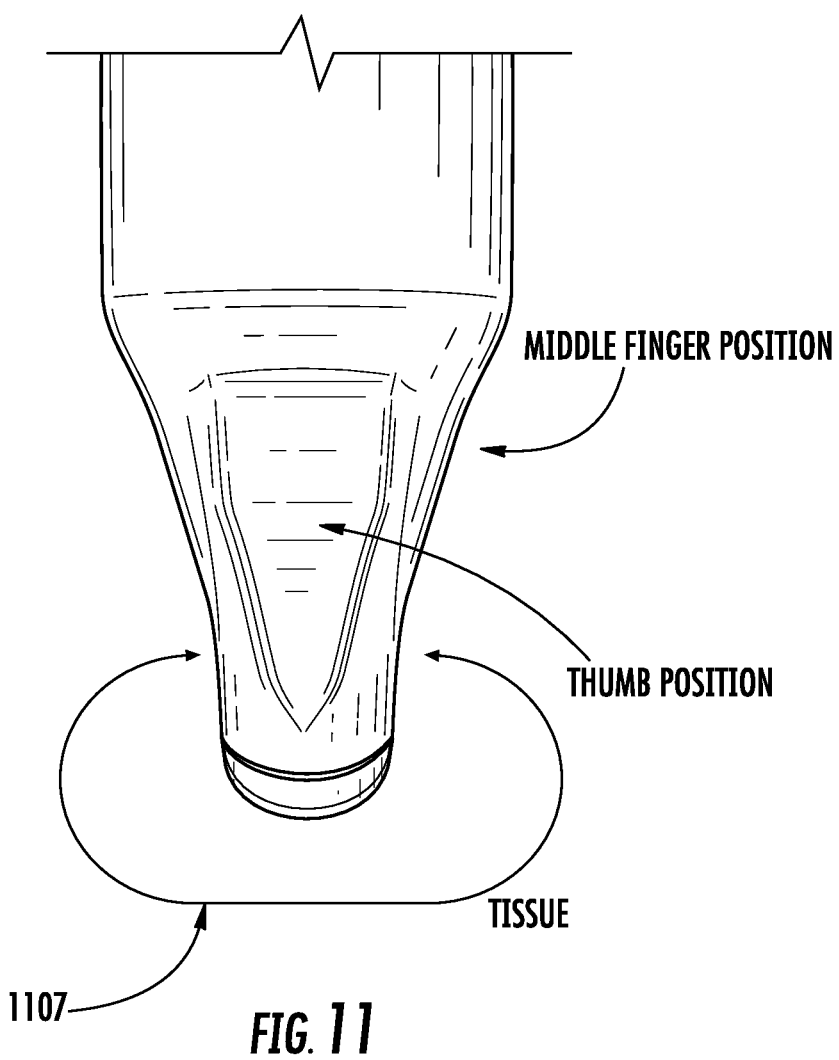
FIG. 11 shows a view of a tip of the oximeter device from above.

FIG. 11 shows a view of a tip of the oximeter from above. This view shows what a user (e.g., a doctor, surgeon, clinician, medical professional, or other user) will see from above while gripping the device. The tip takes up a relatively small amount of area, and the user will have a relatively large unobstructed, clear view 1107 of the tissue. Referring to FIG. 9, the grip locations for the thumb and middle finger are positioned so the fingers and hand also do not obstruct the view. The index finger is against a side of the device, while the ring finger and pinky are point away from the sensor head, toward the back of the device.

A display head upon which the built-in screen is positions is angled with respect to the tubular portion of the body and tip portion, so the user can easily view the screen and the tissue being measured at the same time from a variety of viewing angles during use. The angle of the tubular portion of the device (e.g., which slopes in the hand on the webbing between the thumb and index finger) is also selected to allow for ease in viewing by the user.

Figure 12:
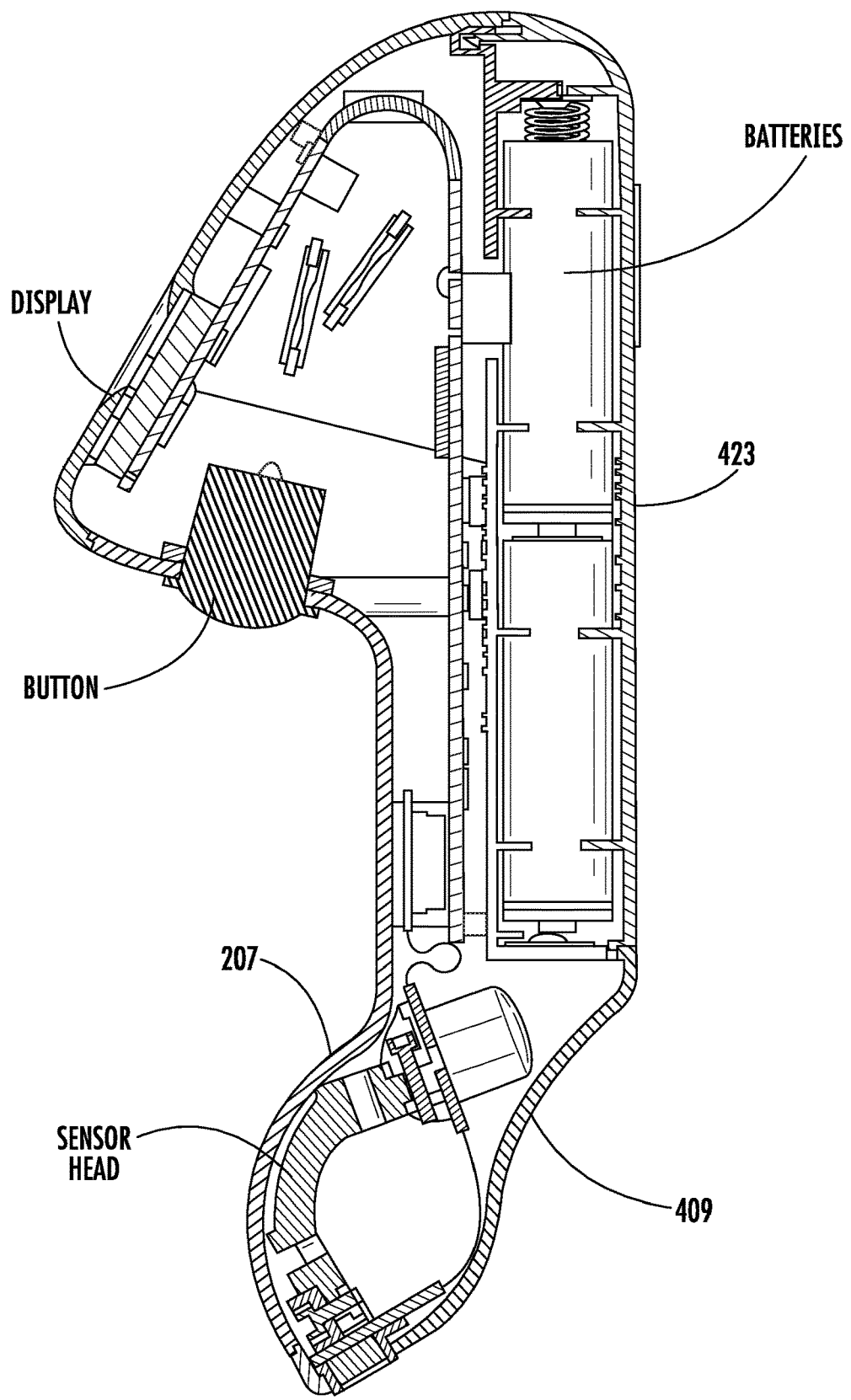
FIG. 12 shows a cutaway view of the oximeter device.

FIG. 12 shows a cutaway view of the oximeter. There is a sensor head assembly, display, button, and batteries. A large percentage of the weight of the device is due to the batteries. The batteries are positioned along a back spine of the device. So, when gripped by the hand, the weight of the device is held by the middle finger. And the back of the device and weight of the batteries of rest against the webbing between the thumb and index finger. The weight of the device is balanced on the hand, so that the user can easily and comfortable use and move the device. The weight should not be against the sensor head, since this may put too much pressure against the tissue which can cause a faulty reading because the blood flow to the tissue may be restricted.

Referring to FIG. 4, the device has an oximeter sensor 422 at its tip. The sensor has sources and detectors. Sources emit light while detectors detect light. The sensor can have various arrangements of sources and detectors.

Figure 13:
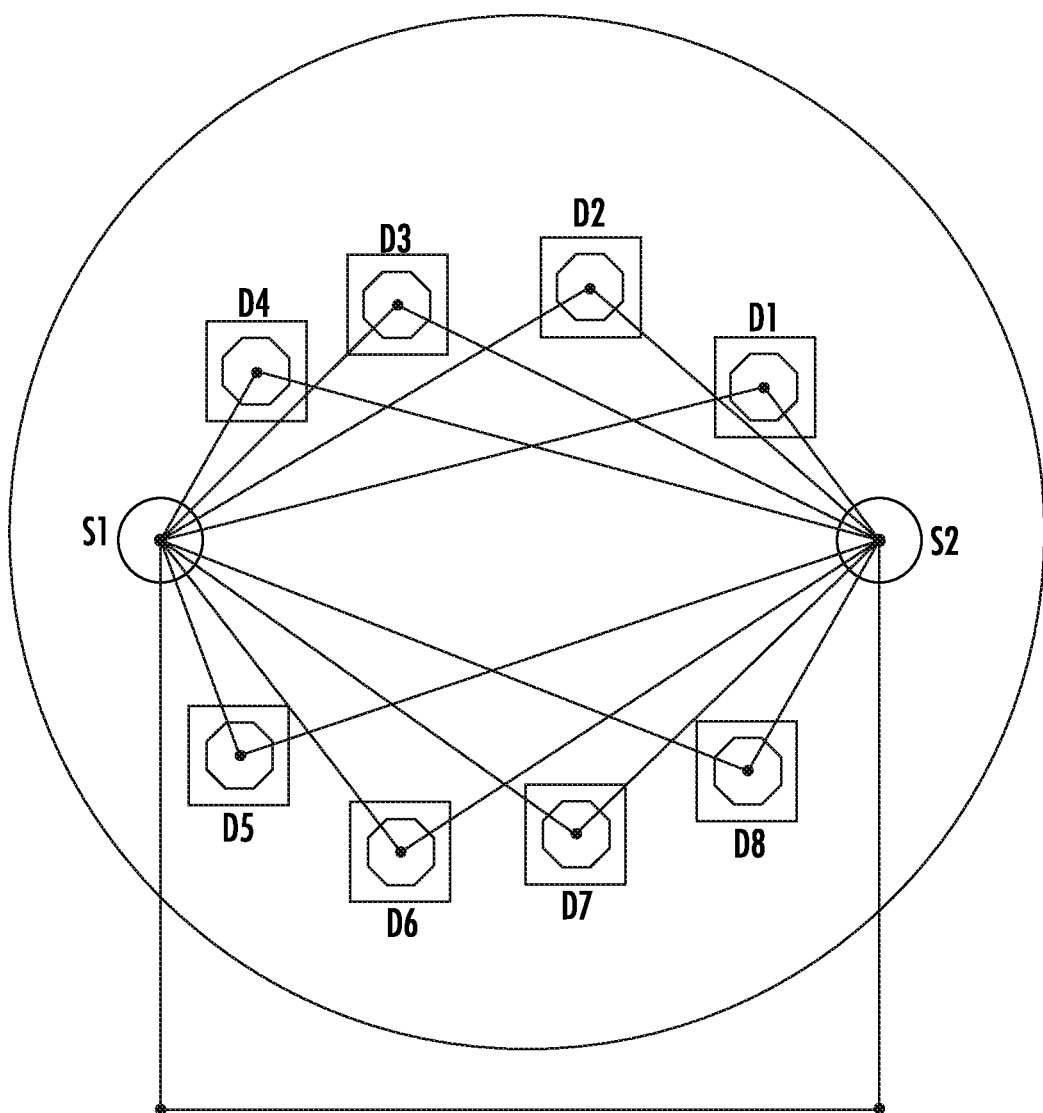
FIG. 13 shows an example of an oximeter sensor with an arrangement sources and detectors.

FIG. 13 shows an example of an oximeter sensor with a specific arrangement sources and detectors. In this implementation, there are two sources and eight detectors. There are eight unique source-detector distance pairs. As discussed, there can be various arrangements of sources and detectors, with more or fewer source and detectors, and source-detector distances.

The source structures and detector structures can be arranged at various positions on the sensor surface to give the distances desired. For example, the two sources form a line, and there are equal number of detectors above and below this line. And the position of a detector (on one side, e.g., above, of the line) will have point symmetry with another detector (on the other side, e.g., below, of the line) about a selected point on the line of the two sources. As an example, the selected point may be the middle between the two sources, but not necessarily. In other implementations, the positioning can be arranged based on a shape, such as a circle, an ellipse, an ovoid, randomly, triangular, rectangular, square, or other shape.

An enclosure of the oximeter has a number of panels, which are attached together at various seam lines shown in the drawings. In an implementation, the enclosure has four panels (e.g., four plastic shells). The panels are made of a plastic material, thermoplastic, resin, acetal homopolymer resin, acetal copolymer, or other polymer.

A back panel 423 is removable so a user can access the batteries, such as to replace the batteries. In an implementation, the batteries are not replaceable. Further, the back panel can be removed to access a data port, which is underneath the batteries. This data port may have a proprietary connector, or can be serial port, universal serial port, or other standard port interface. The user can connect a cable to the data port and download data stored by the oximeter, such as oxygen saturation or other measurements. Also, the port can be used to update the software or firmware of the device.

This application describes some examples of implementations with specific dimensions, measurements, and values. These are not intended to be exhaustive or to limit the invention to the precise form described.

Figure 14:
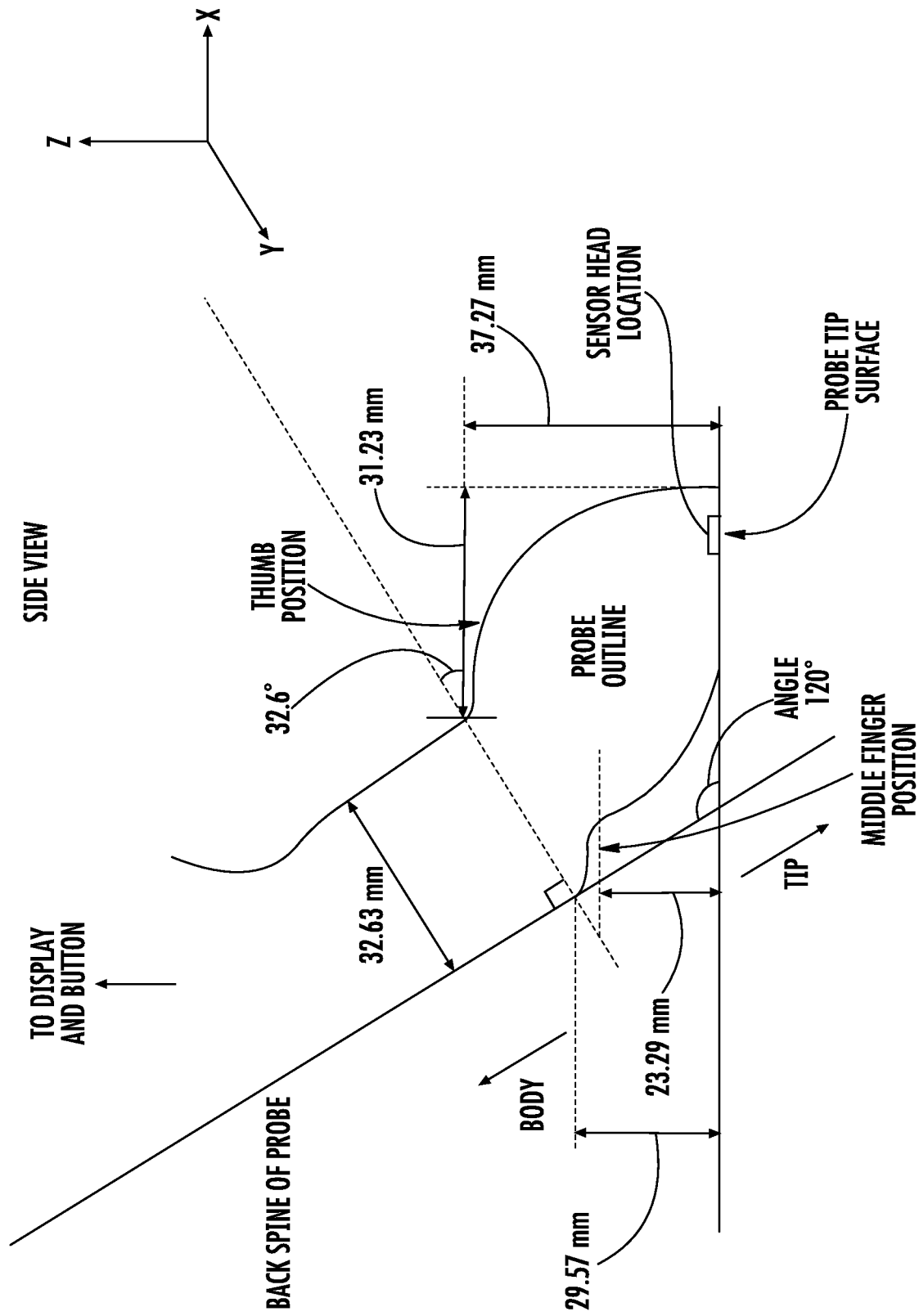
FIG. 14 shows a side view of a tip portion of an oximeter device with measurements and angles.
Figure 15:
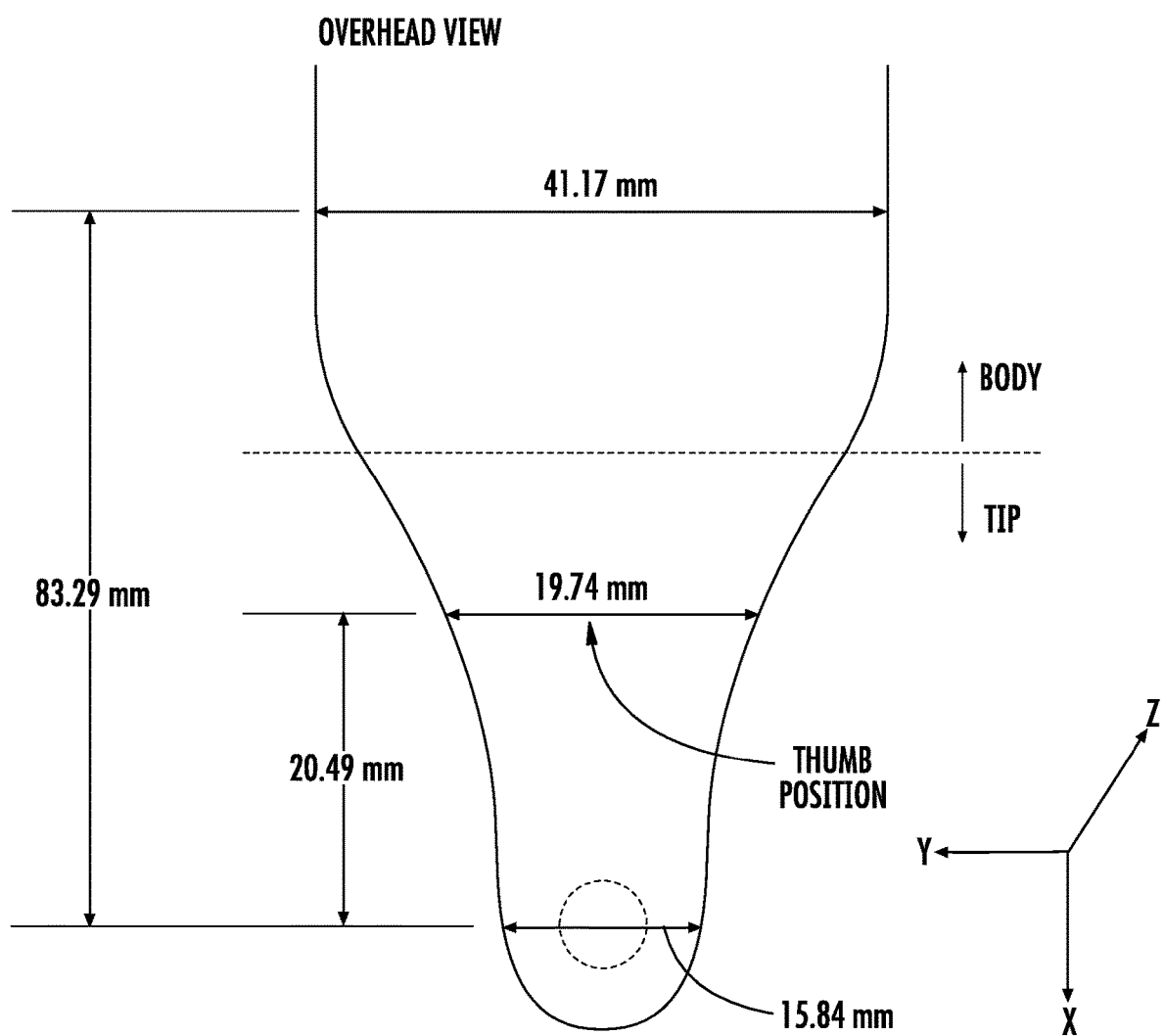
FIG. 15 shows an overhead view of a tip portion of an oximeter device with measurements.

FIG. 14 shows a side view of a tip portion of an oximeter with measurements and angles. FIG. 15 shows an overhead view of a tip portion of an oximeter with measurements. The measurements are in millimeters and angles are in degrees and are approximate values. The values can vary due to, for example, measurement or manufacturing tolerances or other factors (e.g., plus or minus 5 percent, plus or minus 10 percent, plus or minus 15 percent, or plus or minus 20 percent). Further, the measurements are for a specific implementation of the device, and other implementations can have different values, such as certain dimensions made longer to accommodate larger hands.

For the specific implementations described, some specific values, ranges of values, and numbers are provided. These values indicate, for example, dimension, angles, ranges, frequencies, wavelengths, numbers, and other quantities (e.g., numbers of sensors, sources, detectors, diodes, fiber optic cables, domes, and so forth). Some measurements are for a specific implementation of the device, and other implementations can have different values, such as certain dimensions made larger for a larger-sized product, or smaller for a smaller-sized product. The device may be made proportionally larger or smaller by adjusting relative measurements proportionally (e.g., maintaining the same or about the same ratio between different measurements). In various implementations, the values (or numbers or quantities) can be the same as the value given, about the same of the value given, at least or greater than the value given, or can be at most or less than the value given, or any combination of these. The values (or numbers or quantities) can also be within a range of any two values given or a range including the two values given.

The oximeter has a body portion and a tip portion. The tip portion is distal to the body. The body as a back panel or back spine surface, which is relatively flat surface. Opposite the back spine is a relatively flat front surface which is attached to the back spine via to two relatively flat side surfaces. A cross section of this body portion has a generally rectangular shape (with dimensions of about 32.63 millimeters by 41.17 millimeters) with rounded corners. In other implementations, the cross section may be circular, elliptical, triangular, square, pentagonal, hexagonal, octagonal, or any other polygonal shape with any number of sides or facets (e.g., 7, 9, 10, 11, 12, or more).

The thumb rest position extends from the body at an angle of about 32.6 degrees and provides a surface against which the thumb can rest. A length of the thumb rest is about 15 millimeters (x direction), and gradually curves downward toward the tip (which extends a total length from the body about 31.23 millimeters). The thumb rest is about 37.27 millimeters (z direction) above a bottom face of oximeter. The bottom face of the oximeter is relatively flat and has the sensor head, that is formed relatively flush with the bottom face. An angle between the bottom face and back spine of the oximeter is about 120 degrees. Referring to FIG. 15, the thumb rest is about 20.49 millimeters (x direction) offset from an opening for the sensor head.

The middle finger rest is below the body and thumb rest. The middle finger rest has a surface about 23.29 millimeters (z direction) above the bottom face. The thumb and middle finger rests may also be referred to as edges, shelves, ridges, grips, holds, landings, and others.

The display head is angled to allow the user to view the built-in screen from a wide range of viewing angles. In an implementation, the display head is angled from about 30 degrees relative to the back spine surface. In other implementations, the angle can vary from about 10 to about 60 degrees.

Figure 16:
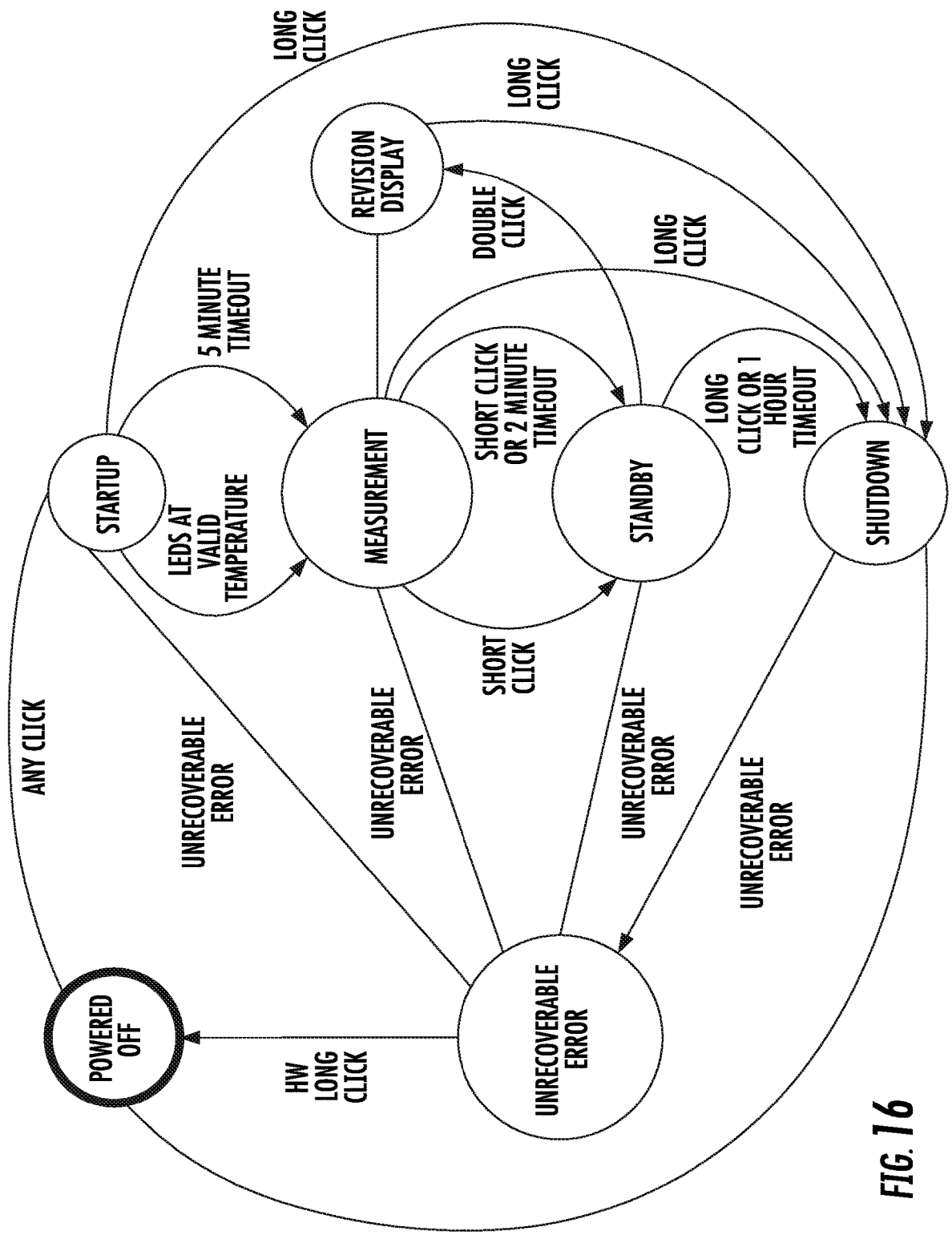
FIG. 16 shows a mode transition or state diagram for an operation of the oximeter device.

FIG. 16 shows a mode transition or state diagram for an operation of the oximeter. FIGS. 17-21 show sample screens that can be displayed on the oximeter screen during the various modes of operation of the device. In an implementation, the oximeter screen is a liquid crystal display (LCD). In other implementation, other display technologies such as light emitting diode (LED) or organic light emitting diode (OLED) may be used.

To access the various modes, the oximeter is operated by way of its single button. The button is used to turn on the device. Table A lists some types of button click operations.

TABLE A

| Type of Button Operation | User Action |
| --- | --- |
| Short Click | User presses button for <2 seconds |
| Double Click | Two short clicks within 750 milliseconds |
| Long Click | User presses button for >2 seconds and <than 12 seconds |
| Hardware Long Click | User presses and holds button for >12 seconds |
| Inactivity | No valid StO2 numbers, no user clicks |

The system modes of FIG. 16 is described in table B. Table B also describes what will be displayed on the device's screen and the information of data that will be logged by the device. The logged data is stored in memory of the device, and can be downloaded by access to the data port described above.

TABLE B

| Mode | Description | LCD | Logging |
| --- | --- | --- | --- |
| Startup | The system enters Startup mode when the system is off and the user clicks | Test Pattern Improper shutdown message if appropriate Splash screen with | Data Log Revision numbers with timestamp Error Log |

TABLE B-continued

| Mode | Description | LCD | Logging |
|---|---|---|---|
| | the power button. The system powers up and operations begin. | warm-up countdown timer that persists until LED ambient temperature is in valid range or for 5 minutes, whichever is shorter. | Revision numbers with timestamp Errors |
| Measurement | After Startup mode activities are complete, the system starts StO2 measurements if possible. If not possible a warning is displayed. | Operating time StO2 numeric value or dashes Low battery icon if appropriate (Note, no battery icon appears until the low battery condition exists, battery <5.3 V) Warnings if appropriate— see separate table | Data Log Data values and StO2 results per separate list Error Log Errors |
| Standby | The system enters Standby mode from Measurement mode either manually if the user short-clicks once or automatically after 2 minutes of inactivity (no valid StO2 values and no user clicks). StO2 calculations cease, but LEDs remain powered to maintain temperature. Data logging is not performed. A short click returns the system to Measurement mode. | Same as Measurement mode, but LCD backlight is off, and dashes are always displayed since StO2 calculations are not performed. | Data Log None Error Log Errors |
| Revision Display | If the user double clicks in Standby mode, SW and FW revision numbers are displayed on LCD. A short click returns the user to Measurement mode. | SW and FW Revision Numbers | Data Log None Error Log Errors |
| Unrecoverable Error | If an unrecoverable error occurs in any other mode, a partial SW-mediated shutdown occurs and ends with an appropriate error message displayed on the LCD. The user must press and hold the power button to power down. See separate table of unrecoverable errors. | Unrecoverable error message (see table) | Data Log Log is flushed to flash Error Log Unrecoverable error Log is flushed to flash |
| Shutdown | From any other mode except Unrecoverable Error, pressing and holding the power button more than 2 seconds (long click) initiates a SW-mediated graceful shutdown and power down. | Shutting down message: Line 1: "Shutting down . . . " Log is flushed to flash Line 3: Release button" | Data Log Log is flushed to flash Error Log Errors |

TABLE B-continued

| Mode | Description | LCD | Logging |
|---|---|---|---|
| | If the SW-mediated shutdown is unsuccessful, the user can press and hold the power button for at least 12 seconds to force a hard shut down. It is likely that this action will corrupt operating time, data log data and error log data, and will cause an Improper Shutdown message at the next power-up. | | |

Table C describes mode modifiers that change or supplement system behavior in the various system modes listed earlier.

TABLE C

| Modifier | Description | LCD | Logging |
|---|---|---|---|
| Communications Modifier | If commanded to do so by an external PC, the system enters communications mode, where all loggings ceases and no StO2 calculations are performed. This allows data to be transferred to and from the system and the external PC. This type of operation is intended for manufacturing calibration and for downloading data and error logs from the device. | Same as current mode. If in Measurement mode, the Communications mode indicator text "COMM MODE" added to the LCD. | Date Log None Error Log None No logging is done so a new unit can be initialized during manufacturing without consuming flash log space. |
| Engineering/ Lab Modifier | If commanded to do so by an external PC, the system enters Engineering/Lab mode. Supplemental information may be displayed on the LCD, data logging may increase and warning precedence may be modified. This type of operation is intended for lab testing and for manufacturing calibration. | Same as current mode. If in Engineering mode, the Communications mode indicator text "ENG MODE" added to the LCD. Supplemental information may be displayed. | |

Figure 17:
FIG. 17 shows a splash screen of the oximeter device.

FIG. 17 shows a splash screen and a 5 minute countdown timer.

Figure 18:
FIG. 18 shows a measurement mode screen of the oximeter device.

FIG. 18 shows a measurement mode screen with a valid StO2 reading and elapsed operating time.

Figure 19:
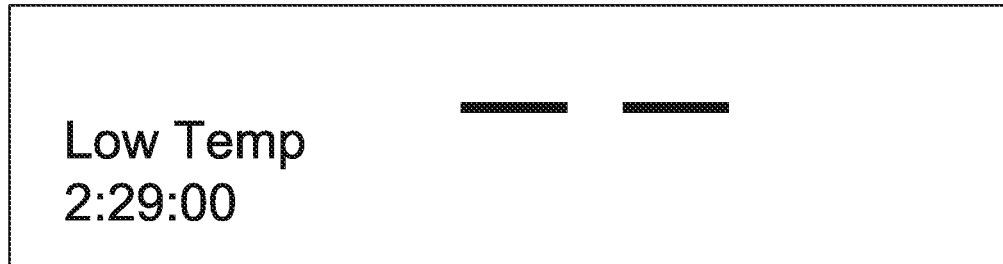
FIG. 19 shows another measurement mode screen.

FIG. 19 shows a measurement mode screen with a "Low Temp" warning, invalid StO2 reading, and elapse operating time.

Figure 20:
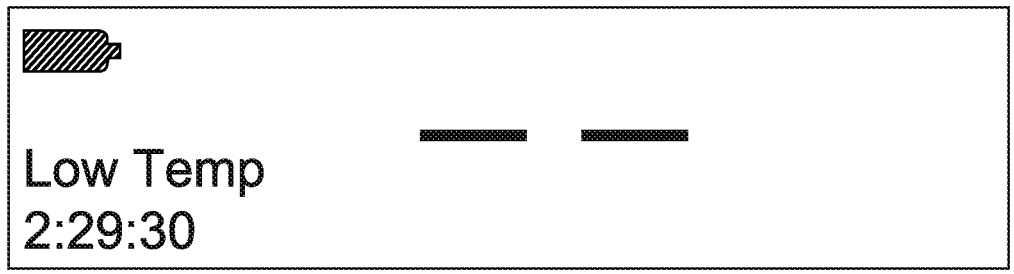
FIG. 20 shows another measurement mode screen.

FIG. 20 shows a measurement mode screen with a low battery warning (battery icon flashes at about 1 hertz), low temperature warning, and invalid StO2 reading.

Figure 21:
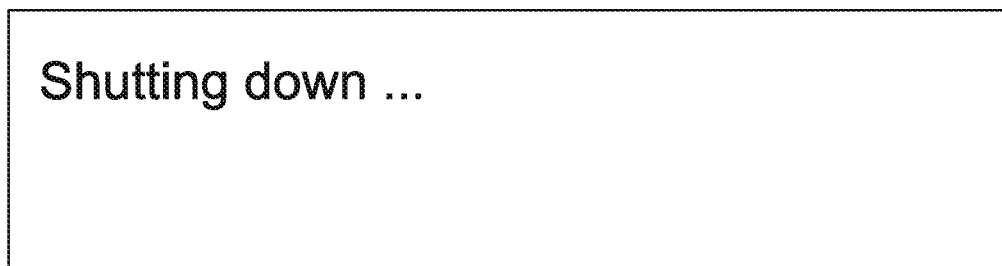
FIG. 21 shows a shutdown screen of the oximeter device.

FIG. 21 shows a screen indicating a shutdown is in process. In an implementation, the message can be "Shutting Down . . . Release Button."

For a specific implementation, table D lists some logging frequencies for data logged in measurement mode.

TABLE D

| | |
|---|---|
| Optical detector magnitude data and StO2 result | Per interrupt, 1 to 3 hertz |
| Temp1 and Temp2 thermistor data | About 1 hertz |
| CPU internal temperature | About ⅓ hertz |
| ADC Maximums | About ⅓ hertz or if saturated |
| ADC Minimums | About ⅓ hertz or if saturated |
| Battery Voltage | About ⅓ hertz |

A clinical data log capacity is approximately 4.8 hours assuming 3 hertz interrupts and no saturation. If saturated, then log analog to digital converter (ADC) maximums and minimums at 1-3 hertz.

Table E lists some warning messages.

TABLE E

| Condition | LCD Message | Impact | Corrective Action |
|---|---|---|---|
| Flash data log is full (for clinicals only, not in product) | Data Full | No further data logging. StO2 measurements continue. | For clinical study, users should stop collecting data and get another device. |
| LEDs >45 degrees Celsius | MAX TEMP | LED powers set to zero and StO2 invalid, dashes displayed until condition no longer exists. LED power levels restored when condition no longer exists. | Shut down the device |
| LEDs >37.5 degrees Celsius | High Temp | StO2 invalid, dashes displayed until condition no longer exists | Move the device to a cooler area until condition no longer exists |
| LEDs <36.5 degrees Celsius | Low Temp | StO2 invalid, dashes displayed until condition no longer exists | Move the device to a cooler area until condition no longer exists |
| Detector saturation | Saturated | StO2 invalid, dashes displayed until condition no longer exists | Correct sensor head placement to improve tissue contact |
| Too much ambient light | Ambient | StO2 invalid, dashes displayed until condition no longer exists | Shield the sensor head from ambient light. |

In an implementation, only one warning message can be displayed at a time, so the following warning order of precedence applies.

Clinical Operation Warning Precedence
1. LEDs greater than 45 degrees Celsius
2. Flash data log full (will be removed for product)
3. High Temp or Low Temp (36.5 degrees Celsius to 37.5 degrees Celsius)
4. Detector saturation
5. Too much ambient light Table F lists some other error messages.

TABLE F

| Condition | LCD Message | Description |
|---|---|---|
| Improper shutdown | Improper Shutdown Logs/Time Corrupted | Message seen at power-up after a hard shut down. Device still measures StO2, but logged data and operating time are corrupted. |
| Algorithm data could not be read from flash successfully | Missing Calibration (Hex code) | A read error or checksum error occurred when attempting to read algorithm data from flash. The hex code indicates the offending item. |

In an implementation, a device includes a body portion and tip portion. The body portion includes a rectangular tubular portion including a front side surface and a back side surface, connected together by first and second side surfaces. The tip portion includes: A first finger rest surface is connected to the front side surface, where the first finger rest surface is a convex surface that extends at a first angle in a first turn direction relative to the front side surface. A front tip surface is connected to the first finger rest surface, where the front tip surface extends at a second angle in a second turn direction relative to the first finger rest surface.

A bottom face surface is connected to the front tip surface, where the bottom face surface extends at a third angle in the second turn direction relative to the first finger rest surface. The bottom face surface includes an opening which will retain a sensor head of the device. A second finger rest finger is connected to the back side surface, where the second finger rest surface is a concave surface that extends at a fourth angle in the first turn direction relative to the back side surface. A back tip surface is connected between the second finger rest surface and the bottom face surface, where the back tip surface is a convex surface that extends at a fifth angle in the first turn direction relative to the second finger rest surface.

The back side and bottom face surfaces are relatively flat surfaces that are angled relative to each other in a range from 90 degrees to about 150 degrees. A first height of the first finger position above the bottom face surface is greater than a second height of the second finger position above the bottom face surface. The first angle is angled relative to the front side surface in a range from 90 degrees to about 60 degrees.

Batteries are enclosed within the rectangular tubular portion, and the batteries are closer to the back side surface than the front side surface. The rectangular tubular portion includes rounded corners. The first finger rest surface is adapted for a thumb of a user. The second finger rest surface is adapted for a middle finger of a user. When the device is gripped by a hand of a user, a thumb of the user will be against the first finger rest surface, a middle finger of the user will be against the first finger rest surface, and a webbing between the thumb and a index finger of the user will be against the back side surface.

The sensor head includes a number of sources and a number of detectors. The sources are arranged along a line. There are an equal number of detectors on either side of this line. A position of a detector on a first side of the line will have point symmetry with another detector on a second of the line about a selected point on the line. The selected point is a middle or midpoint between two sources. A first distance between the first and second side surfaces is greater than a second distance between the front and back side surfaces.

An oximeter system can include or incorporate the device described. In an implementation, the oximeter system is a pulse oximeter system. In an implementation, the oximeter system is a tissue oximeter system or reflective oximeter system.

For a pulse oximetry: At the measuring site there are constant light absorbers and scatterers that are always present. They are skin, tissue, venous blood, and the arterial blood. There is also a time varying component of the light signal that is primarily due to absorption that is a result of an increase in arterial blood volume across the measuring site. This results in more light absorption during the surge. A pulse oximeter measures the absorption at the peak of the pulse and subtracts out the baseline to isolate the absorption of the pulse itself and which is due to the arterial blood absorption and calculation the pulsatile arterial saturation.

For tissue oximetry: the Intra.Ox looks at the constant light absorbers and scatterers, measuring the tissue saturation trend which is primarily due to a combination of both the arterial and venous saturations changes over time scales longer than the pulsatile part.

The device can include: batteries, enclosed within the rectangular tubular portion, where the batteries are closer to the back side surface than the front side surface; sensor head including an arrangement of source structures and detector structures; a display; and electronics, connected to the battery, sensor head, and display. The electronics cause light to be transmitted through the source structures of the sensor head, and based on light received through the detector structures, the electronics determines an oxygen saturation value and causes the display to show the oxygen saturation value.

The device can include a sensor head assembly including or incorporating the sensor head. The sensor head assembly is enclosed by a space between the convex surface of the first finger rest surface and the concave surface of the second finger rest surface.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
a body portion comprising a front side surface and a back side surface, coupled together by first and second side surfaces; and
a tip portion comprising:
a first finger rest surface, coupled to the back side surface, wherein the first finger rest surface is a concave surface that extends at a first angle in a first turn direction, relative to the back side surface;
a back tip surface, coupled between the first finger rest surface and a bottom face surface, wherein the back tip surface is a convex surface that extends at a second angle in a first turn direction relative to the first finger rest surface; and
the bottom face surface, coupled between the back tip surface and the front side surface, wherein the bottom face surface extends at a third angle in a first turn direction relative to the first finger rest surface, the bottom face surface comprises a sensor head, and the sensor head comprises a surface visible from an exterior of the device,
a first line, longitudinally extending along the back side surface of the body portion, does not pass through the tip portion, and
a second line, extending transverse to and through the surface of the sensor head, does not pass through the back side surface,
wherein the back side and the bottom face surface have a fixed, nonadjustable angle relative to each other.

2. The device of claim 1 wherein the tip portion comprises:
a second finger rest surface, coupled between the front side surface and the bottom face surface, wherein the second finger rest surface is a concave surface that extends at a fourth angle, relative to the front side surface, in the first turn direction.

3. The device of claim 2 wherein the tip portion comprises:
a front tip surface, coupled to the second finger rest surface, wherein the front tip surface extends at a fifth angle in a second turn direction relative to the first finger rest surface.

4. The device of claim 2 wherein a first finger position is associated with the first finger rest surface, a second finger position is associated with the second finger rest surface, and a first height of the first finger position above the bottom face surface is less than a second height of the second finger position above the bottom face surface.

5. The device of claim 2 wherein the second finger rest surface is adapted for a thumb of a user.

6. The device of claim 2 wherein when the device is gripped by a hand of a user,
a middle finger of the user will be against the first finger rest surface,
a thumb of the user will be against the second finger rest surface, and
a webbing between the thumb and an index finger of the user will be against the back side surface.

7. The device of claim 1 wherein the body portion comprises a rectangular shape with rounded corners.

8. The device of claim 1 wherein the first finger rest surface is adapted for a middle finger of a user.

9. The device of claim 1 wherein the sensor head comprises:
a plurality of sources, the sources are arranged along a third line; and
a plurality of detectors, wherein there are an equal number of detectors on either side of the third line, and a position of a detector on a first side of the third line will have point symmetry with another detector on a second side of the third line about a selected point on the third line.

10. The device of claim 9 wherein the selected point is at a middle between two sources.

11. The device of claim 1 wherein a first distance between the first and second side surfaces is greater than a second distance between the front and back side surfaces.

12. An oximeter system comprising the device of claim 1.

13. The device of claim 1 comprising:
a display, coupled to the body portion; and
electronics, housed in the body portion and coupled to the sensor head and the display.

14. The device of claim 13 wherein the electronics cause light to be transmitted through source structures of the sensor head, and based on light received through detector structures, the electronics determines an oxygen saturation value and causes the display to show the oxygen saturation value.

15. The device of claim 13 comprising:
at least one battery, enclosed within a rectangular tubular portion, wherein the battery is closer to the back side surface than the front side surface.

16. The device of claim 1 wherein the body portion comprises a rectangular shape with rounded corners.

17. The device of claim 1 wherein when the sensor head is configured to be placed against a tissue to make a medical measurement, the back side surface is closer to the tissue than front side surface.

18. The device of claim 1 wherein when the sensor head is configured to be placed against a tissue to make a medical measurement, the back side surface faces toward the tissue.

19. The device of claim 1 wherein when the sensor head is configured to be placed against a tissue to make a medical measurement, the back side surface faces toward the tissue and the front side surface faces away from the tissue.

20. The device of claim 1 wherein the bottom face surface faces towards the first line.

21. The device of claim 1 wherein the surface of the sensor head faces towards the first line.

22. A device comprising:
a body portion comprising a front side surface and a back side surface, coupled together by first and second side surfaces; and
a tip portion comprising:
a first finger rest surface, coupled to the back side surface, wherein the first finger rest surface is a concave surface that extends at a first angle in a first turn direction, relative to the back side surface;
a back tip surface, coupled between the first finger rest surface and a bottom face surface, wherein the back tip surface is a convex surface that extends at a second angle in a first turn direction relative to the first finger rest surface;
the bottom face surface, coupled between the back tip surface and the front side surface, wherein the bottom face surface extends at a third angle in a first turn direction relative to the first finger rest surface,
the bottom face surface comprises a sensor head, comprising a surface visible from an exterior of the device and an arrangement of source structures and detector structures,
a first line, longitudinally extending along the back side surface of the body portion, does not pass through the tip portion, and
a second line, extending transverse to and through the surface of the sensor head, does not pass through the back side surface;
wherein the back side and the bottom face surface have a fixed, nonadjustable angle relative to each other;
a display, coupled to the body portion; and
electronics, housed in the body portion and coupled to the sensor head and the display, wherein the electronics cause light to be transmitted through the source structures of the sensor head, and based on light received through the detector structures, the electronics determines an oxygen saturation value and causes the display to show the oxygen saturation value.

23. The device of claim 22 wherein the sensor head comprises:
a plurality of sources, the sources are arranged along a line; and
a plurality of detectors, wherein there are an equal number of detectors on either side of this line, and a position of a detector on a first side of the line will have point symmetry with another detector on a second side of the line about a selected point on the line,
on the first side of the line, a first distance is between a first detector and a second detector,
on the first side of the line, a second distance is between a second detector and a third detector, and
the first distance is different from the second distance.

24. The device of claim 22 wherein the tip portion comprises:
a second finger rest surface, coupled between the front side surface and the bottom face surface, wherein the second finger rest surface is a concave surface that extends at a fourth angle, relative to the front side surface, in the first turn direction.

25. The device of claim 22 wherein when the sensor head is configured to be placed against a tissue to make a medical measurement, the back side surface is closer to the tissue than front side surface.

26. The device of claim 22 wherein when the sensor head is configured to be placed against a tissue to make a medical measurement, the back side surface faces toward the tissue.

27. The device of claim 22 wherein when the sensor head is configured to be placed against a tissue to make a medical measurement, the back side surface faces toward the tissue and the front side surface faces away from the tissue.

28. The device of claim 22 wherein the bottom face surface faces towards the first line.

29. The device of claim 22 wherein the surface of the sensor head faces towards the first line.

30. A device comprising:
a body portion comprising a front side surface and a back side surface, coupled together by first and second side surfaces; and
a tip portion comprising:
a first finger rest surface, coupled to the back side surface, wherein the first finger rest surface is a concave surface that extends at a first angle in a first turn direction, relative to the back side surface;
a back tip surface, coupled between the first finger rest surface and a bottom face surface, wherein the back tip surface is a convex surface that extends at a second angle in a first turn direction relative to the first finger rest surface; and
the bottom face surface, coupled between the back tip surface and the front side surface, wherein the bottom face surface extends at a third angle in a first turn direction relative to the first finger rest surface, and the bottom face surface comprises a sensor head,
a first line, longitudinally extending along the back side surface of the body portion, does not pass through the tip portion, and a second line, extending transverse to and through the bottom face surface and does not pass through the back side surface,
wherein the back side and the bottom face surface have a fixed, nonadjustable angle relative to each other.

31. The device of claim 30 wherein the tip portion comprises:
a second finger rest surface, coupled between the front side surface and the bottom face surface, wherein the second finger rest surface is a concave surface that extends at a fourth angle, relative to the front side surface, in the first turn direction.

32. The device of claim 30 wherein the bottom face surface faces towards the first line.

\* \* \* \* \*